United States Patent
Itoh et al.

(10) Patent No.: US 8,096,659 B2
(45) Date of Patent: Jan. 17, 2012

(54) FUNDUS CAMERA

(75) Inventors: Hiroshi Itoh, Yokohama (JP); Shinya Tanaka, Tokyo (JP); Motoya Takai, Nagareyama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/858,244

(22) Filed: Aug. 17, 2010

(65) Prior Publication Data

US 2010/0309431 A1 Dec. 9, 2010

Related U.S. Application Data

(63) Continuation of application No. 12/424,431, filed on Apr. 15, 2009, now Pat. No. 7,798,642.

(30) Foreign Application Priority Data

Apr. 22, 2008 (JP) .................. 2008-110939

(51) Int. Cl.
*A61B 3/10* (2006.01)
*A61B 3/14* (2006.01)
(52) U.S. Cl. ......... 351/206; 351/205; 351/211; 351/221
(58) Field of Classification Search ........... 351/200–246
See application file for complete search history.

(56) References Cited

U.S. PATENT DOCUMENTS

| 4,405,215 | A  | * | 9/1983 | Sano et al. ............... 351/208 |
| 7,347,553 | B2 | * | 3/2008 | Matsumoto ............... 351/214 |
| 7,734,001 | B2 | * | 6/2010 | Saeki ....................... 375/376 |
| 7,736,001 | B2 | * | 6/2010 | Tanaka et al. ............. 351/214 |
| 7,798,642 | B2 | * | 9/2010 | Itoh et al. ................. 351/206 |
| 2010/0141770 | A1 | * | 6/2010 | Gomi ........................ 348/164 |

FOREIGN PATENT DOCUMENTS

JP     2005-279154 A    10/2005

* cited by examiner

*Primary Examiner* — Mohammed Hasan
(74) *Attorney, Agent, or Firm* — Canon U.S.A., Inc., IP Division

(57) ABSTRACT

A fundus camera includes an optical path splitting unit arranged between a focusing unit and an imaging unit. The splitting unit has characteristics adapted to reflect light of a visible light region and to transmit near-infrared light. The splitting unit retreats from an optical path when a still fundus image is photographed. A quick-return mirror having such characteristics is used as the splitting unit. When near-infrared illumination light having a wavelength of about 850 nm is used, such light can be incident upon the imaging unit without loss of the amount of light. Visible light output from an internal fixation target is projected onto a subject's eye. A cornea diaphragm and a crystalline lens diaphragm are used for observing a fundus with invisible light. Each of the cornea diaphragm and crystalline lens diaphragm can be changed to another one having a different diameter.

17 Claims, 6 Drawing Sheets

FUNDUS CAMERA

CROSS REFERENCE TO RELATED APPLICATIONS

The present application is a continuation of U.S. patent application Ser. No. 12/424,431, filed on Apr. 15, 2009, now U.S. Pat. No. 7,798,642 entitled "FUNDUS CAMERA", the content of which is expressly incorporated by reference herein in its entirety. This application also claims priority from Japanese Patent Application No. 2008-110939 filed Apr. 22, 2008, which is hereby incorporated by reference herein in their entirety.

BACKGROUND OF THE INVENTION

1. Field of the Invention

The present invention relates to a fundus camera for observing a fundus of a subject's eye with near-infrared light or visible light.

2. Description of the Related Art

Fundus cameras for observing and photographing a subject's eye fundus are roughly classified into a mydriatic type fundus camera to be used by applying a mydriatic to a subject's eye, and a non-mydriatic type fundus camera to be used without applying a mydriatic to a subject's eye. The former type fundus camera is used mainly by ophthalmologists. Usually, when a subject's eye fundus is photographed using the former type fundus camera, a plurality of images of the fundus is taken not only by a color photographing technique but also by various techniques, such as a fluorescent photographing technique and a special filter photographing technique. The latter type fundus camera is used mainly by doctors for medical check-up or physicians. When a subject's eye fundus is photographed using the latter type fundus camera, single shot photographing is mainly performed.

However, in recent years, needs for non-mydriatic photographing have grown among ophthalmologists, because the application of a mydriatic to a subject's eye can be omitted. Japanese Patent Application Laid-Open No. 9-66030 discusses a dual-use type fundus camera developed to be able to be used for both mydriatic photographing and non-mydriatic photographing, which can photograph both a dilated eye and a non-dilated eye.

The dual-use type fundus camera is provided with an optical finder. In a case where this dual-use type fundus camera is used as a fundus camera of the mydriatic type, an examiner observes a subject's eye fundus with visible light via the optical finder. On the other hand, in a case where the dual-use type fundus camera is used as a fundus camera of the non-mydriatic type, an examiner observes a subject's eye fundus with near-infrared light. A mirror that folds light back to the optical finder retreats to the outside of the optical path. Thus, reflection light from a fundus image is introduced to an imaging unit, such as a charge-coupled device (CCD), so that a fundus image is displayed on a monitor.

Further, the dual-use type fundus camera is configured such that when a subject's eye fundus is photographed, a mirror for splitting an optical path into an observing optical system and a photographing optical system retreats to the outside of the optical path, and that a fundus image is introduced to the imaging unit.

On the other hand, Japanese Patent Application Laid-Open No. 2003-135402 discusses a fundus camera which is not of the dual-use type usable for both mydriatic photographing and non-mydriatic photographing but of the non-mydriatic photographing type. However, this fundus camera is configured to perform both observing and photographing of a subject's eye fundus using a single imaging unit and to have a unit for presenting an internal fixation target. An optical path from a subject's eye is split by an optical path splitting prism into an optical path to the imaging unit and another optical path to the internal fixation target. The optical path splitting prism has characteristics adapted to transmit a part of light having a wavelength of light of the internal fixation target and to reflect light having the other wavelengths.

The dual-use type fundus camera usable for both mydriatic photographing and non-mydriatic photographing, which is discussed in Japanese Patent Application Laid-Open No. 9-66030, requires two components, i.e., a moving-image imaging unit for observing a subject's eye fundus, and a still-image imaging unit for photographing the fundus. Accordingly, the dual-use type fundus camera discussed in Japanese Patent Application Laid-Open No. 9-66030 has problems in that the configuration of the fundus camera is complex, and that the size of the fundus camera is large. In addition, when performing non-mydriatic photographing of a subject's eye fundus, the fundus camera needs an internal fixation target for guiding a line of sight of a subject's eye and for making the subject's eye fixate thereon. That is, the fundus camera requires another additional optical system therefor.

The fundus camera discussed in Japanese Patent Application Laid-Open No. 2003-135402 is configured to use a single imaging unit for both observing and photographing a subject's eye fundus in order to miniaturize the body thereof. Thus, the fundus camera can project an internal fixation target onto a subject's eye. However, the fundus camera requires the optical path splitting prism for splitting the optical path from a subject's eye into an optical path to the imaging unit and another optical path to the internal fixation target. When photographing a subject's eye fundus with visible light, the optical path splitting prism transmits light of wavelengths within a range corresponding to the wavelength of light of the internal fixation target, among the wavelengths of reflection light from the fundus. Thus, not all light reflected from the fundus can be incident on the imaging unit. Consequently, a loss of the amount of light occurs. In addition, no optical finder is provided in the fundus camera. Accordingly, a subject's eye fundus cannot be observed by direct vision.

SUMMARY OF THE INVENTION

The present invention is directed to a fundus camera configured to use a single imaging unit for both observing and photographing a subject's eye fundus, and to be capable of reducing, when photographing the fundus, loss of the amount of light reflected from the fundus, and efficiently indicating an internal fixation target.

According to an aspect of the present invention, a fundus camera includes an illumination unit including an invisible light generating unit configured to irradiate light of an invisible light region for observing a fundus of a subject's eye with invisible light, a visible photographing light generating unit configured to irradiate light of a visible light region for photographing the fundus with visible light, and a near-infrared cut filter configured to be insertable into an optical path during photographing of a still image of the fundus, a focusing unit configured to adjust focus on the fundus based on a reflection image from the fundus illuminated by the illumination unit, an imaging unit configured to capture a fundus image formed from reflection light from the fundus, the imaging unit having sensitivity to both light of the visible light region and light of a near-infrared light region and being capable of outputting a moving image and a still image, an optical path splitting unit located between the focusing unit and the imaging unit, having characteristics of reflecting light of the visible light region and of transmitting near-infrared light, and configured to be retreatable from the optical path during photographing of a still image, and an internal fixation target indicating unit located at a position that is substantially conjugate with a position of the fundus on a reflection optical path of the optical path splitting unit and configured to guide a direction of a line of sight of the subject's eye.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DETAILED DESCRIPTION OF THE EMBODIMENTS

Various exemplary embodiments, features, and aspects of the invention will be described in detail below with reference to the drawings.

Figure 1:
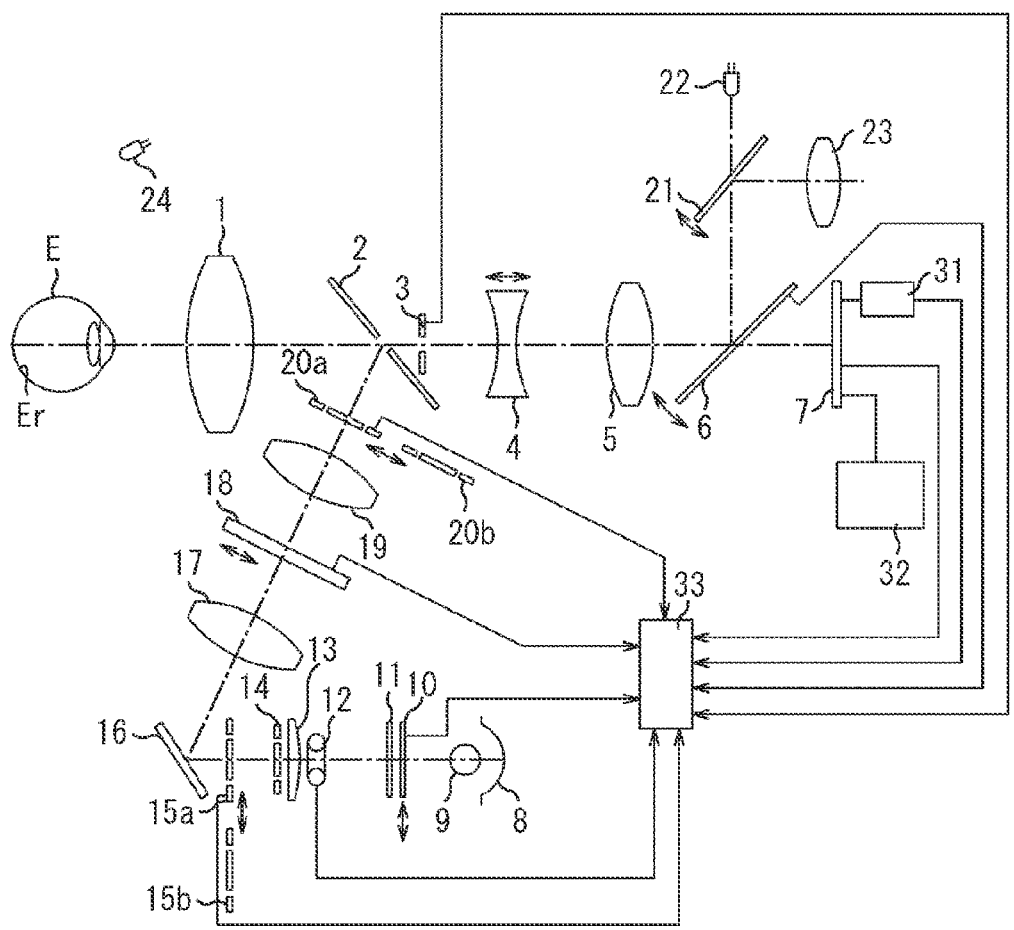
FIG. 1 illustrates a configuration of a fundus camera of the dual-use type usable for both mydriatic photographing and non-mydriatic photographing according to an exemplary embodiment of the present invention.

FIG. 1 illustrates a configuration of a fundus camera of the dual-use type usable for both mydriatic photographing and non-mydriatic photographing according to an exemplary embodiment of the present invention. In an observing/photographing optical system in front of a subject's eye E, an objective lens 1, a perforated mirror 2, a photographing diaphragm 3, a focusing lens 4, an imaging lens 5, a quick-return mirror 6, and an imaging unit 7 are sequentially arranged. The focusing lens 4 is a focusing unit for focusing the optical system on a fundus $E_r$ of the subject's eye E. The quick-return mirror 6 is an optical path splitting unit constructed to be retreatable from an optical path. The imaging unit 7 has sensitivity to both light of a visible light region and near-infrared light of an invisible light region.

An illumination optical system serving as an illumination unit is provided on an incident optical path to the perforated mirror 2. In the illumination optical system, a visible light cut filter 10, a diffusion plate 11, a xenon tube 12, a lens 13, a pupil stop 14, a crystalline lens diaphragm 15a, and a mirror 16 are sequentially arranged in the direction from a halogen lamp 9 towards the perforated mirror 2. A reflecting mirror 8 is located behind the halogen lamp 9. In addition, a relay lens 17, a near-infrared cut filter 18, a relay lens 19, and a cornea diaphragm 20a are sequentially arranged in the reflection direction of the mirror 16.

The halogen lamp 9 is an observing illumination light source. The xenon tube 12 is a photographing light source. The visible light cut filter 10 cuts out light of a visible light region. The near-infrared cut filter 18 cuts out light of a near-infrared light region. Both the visible light cut filter 10 and the near-infrared cut filter 18 can be inserted into and removed from the illumination optical path.

Further, each of the pupil stop 14, the crystalline lens diaphragm 15a, and the cornea diaphragm 20a has an annular opening portion. The crystalline lens diaphragm 15a can be changed to another crystalline lens diaphragm 15b differing in diameter therefrom. Similarly, the cornea diaphragm 20a can be changed to another cornea diaphragm 20a differing in diameter therefrom. When a fundus is observed with invisible light, the cornea diaphragm 20a and the crystalline lens diaphragm 15a are used. On the other hand, when the fundus is observed with visible light, the cornea diaphragm 20b and the crystalline lens diaphragm 15b are used. Observation of the fundus with invisible light and that of the fundus with visible light, which is performed by applying a mydriatic to a subject's eye E, differ from each other in required pupil diameter of the subject's eye E and in angle of view representing a range of a photographed fundus $E_r$ thereof. Thus, such observation techniques can be optimized using the diaphragms 20a, 20b, 15a, and 15b differing in diameter from one another.

On the reflection optical path of the quick-return mirror 6, an oblique mirror 21, which can be inserted into and removed from the optical path, and an internal fixation target 22, which function as an internal fixation target indicating unit, are arranged. The internal fixation target 22 is placed at a position that is substantially conjugate with that of the fundus $E_r$ of the subject's eye E. The wavelength of light of the internal fixation target 22 has a value for guiding the direction of a line of sight of the subject's eye E, e.g., 530 nm. On the reflection optical path of the oblique mirror 21, an optical finder 23 is arranged. Thus, the observing light source is constructed. Further, an external fixation target 24 for performing a fixation guiding operation for the subject's eye E is provided in the front vicinity of the subject's eye E.

A display position correcting unit 31 for correcting a position, and a monitor 32 for displaying a photographed fundus image are connected to the imaging unit 7. An output of the imaging unit 7 is connected to a control unit 33 for controlling the entire system. The photographing diaphragm 3, the quick-return mirror 6, the imaging unit 7, the visible light cut filter 10, the xenon tube 12, the crystalline lens diaphragm 15a, the near-infrared cut filter 18, the cornea diaphragm 20a, and the display position correcting unit 31 are connected to the control unit 33.

Figure 2:
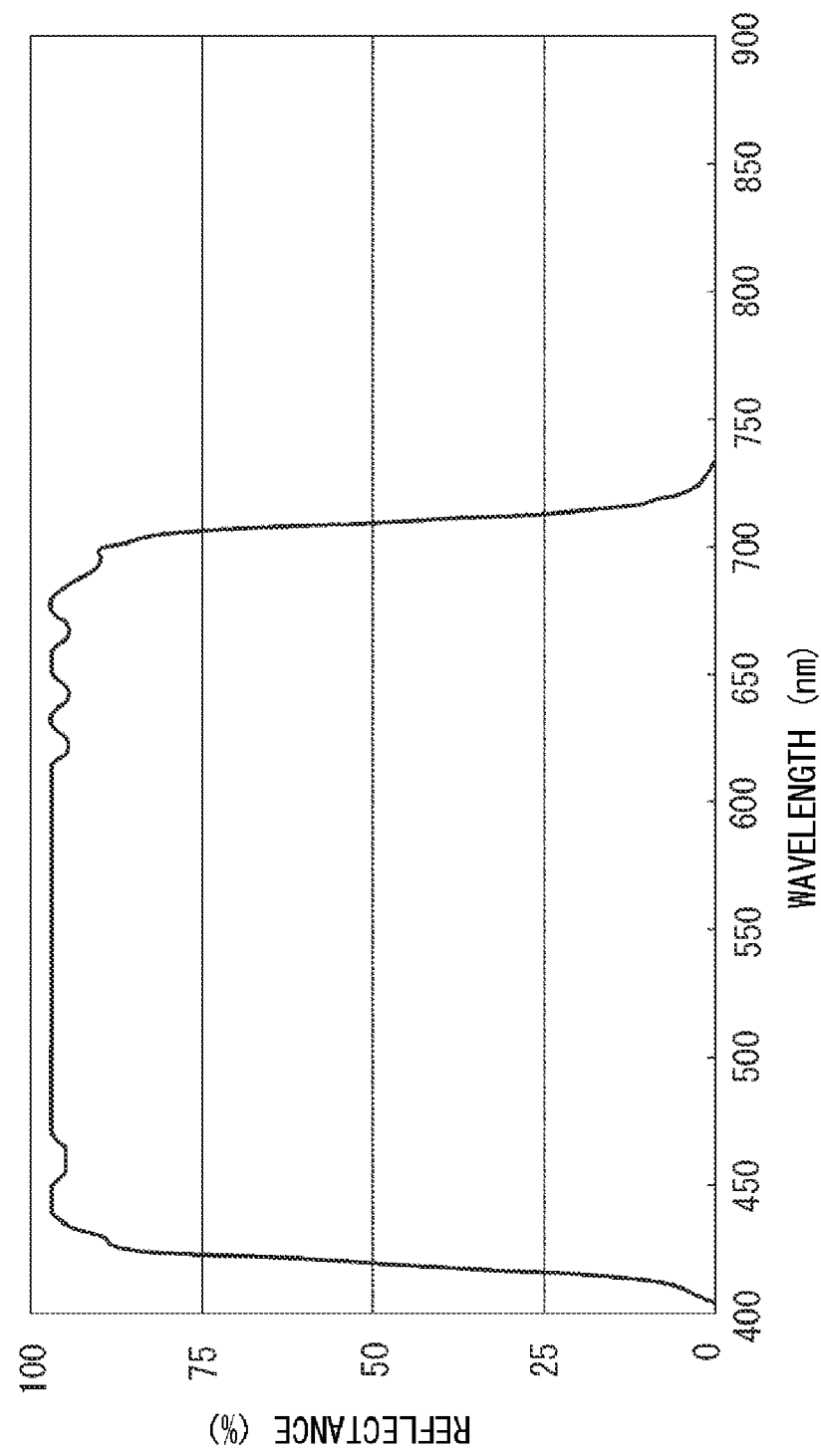
FIG. 2 is a graph illustrating a reflection characteristic of a quick-return mirror in the fundus camera according to an exemplary embodiment of the present invention.

FIG. 2 is a graph illustrating a reflection characteristic of the quick-return mirror 6. The quick-return mirror 6 has characteristics adapted to reflect light of a visible light region and to transmit light of a near-infrared light region. Accordingly, for example, when near-infrared illumination light having a wavelength of about 850 nm is used, such light can be incident upon the imaging unit 7 without causing loss of the amount of light. In addition, visible light irradiated from the internal fixation target 22 is projected onto the subject's eye E.

Figure 3:
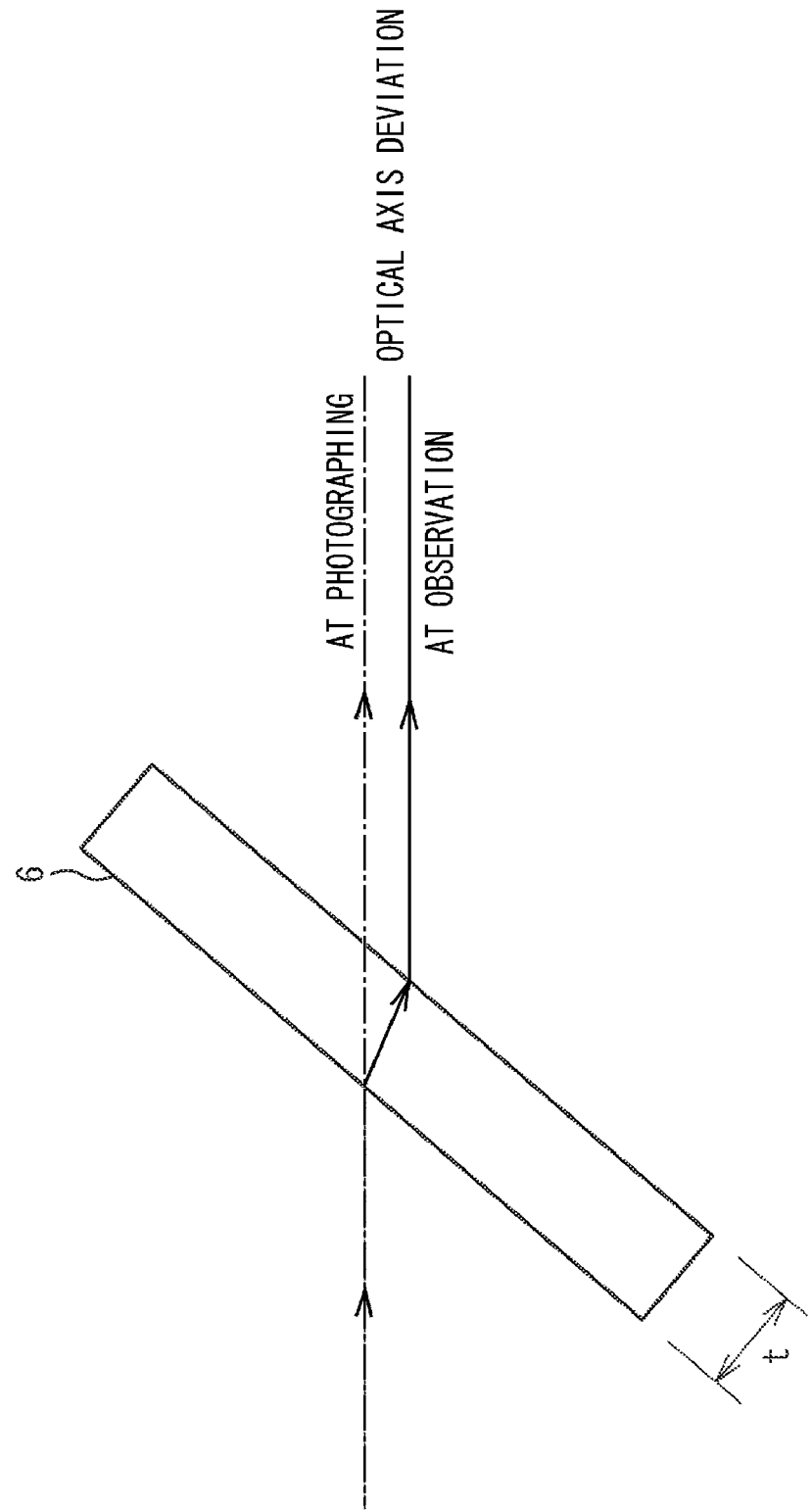
FIG. 3 illustrates an optical axis deviation due to the quick-return mirror in the fundus camera according to an exemplary embodiment of the present invention.

As is described below, in a non-mydriatic mode for observing a fundus $E_r$ with near-infrared light, the quick-return mirror 6 is inserted into the optical path. When the fundus $E_r$ is photographed, the quick-return mirror 6 is withdrawn from the optical path. Consequently, as illustrated in FIG. 3, the position of an optical axis at observation of a fundus $E_r$ deviates from that of the optical axis at photographing of the fundus $E_r$ by a distance corresponding to the thickness t of the quick-return mirror 6. Thus, in the present embodiment, the thickness t of the quick-return mirror 6 is set to be 0.8 mm or less in order to reduce the amount of deviation of the optical axis. Consequently, influence of the deviation of the optical axis can be lessened.

Figure 4:
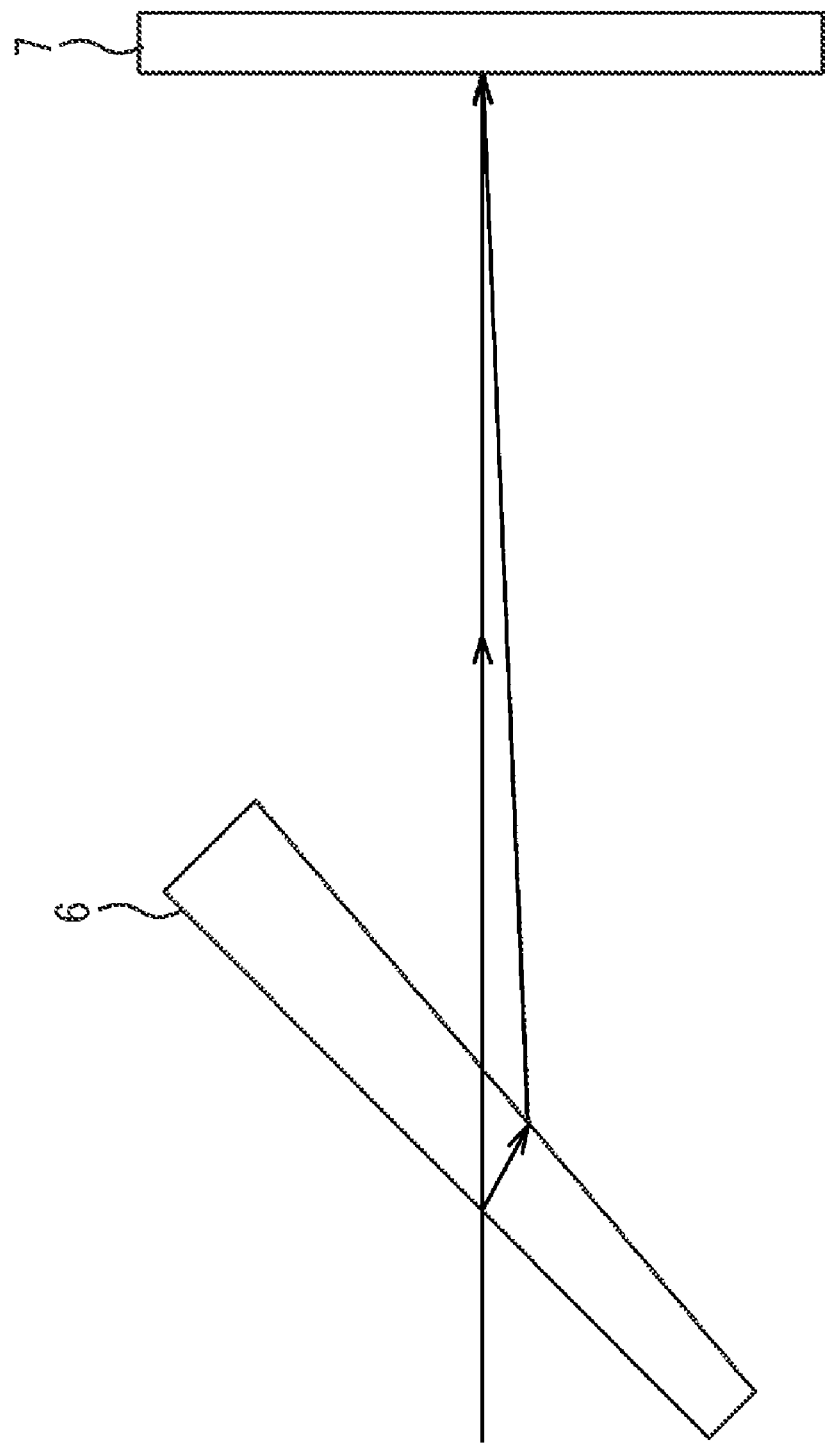
FIG. 4 illustrates a shape of the quick-return mirror in the fundus camera according to an exemplary embodiment of the present invention.

In addition to the reduction in the thickness t of the quick-return mirror 6, for example, it is considered for reducing the amount of deviation of the optical axis that the quick-return mirror 6 is cross-sectionally wedge-shaped, as illustrated in FIG. 4, thereby mitigating the influence of the deviation of the optical axis.

Figure 5:
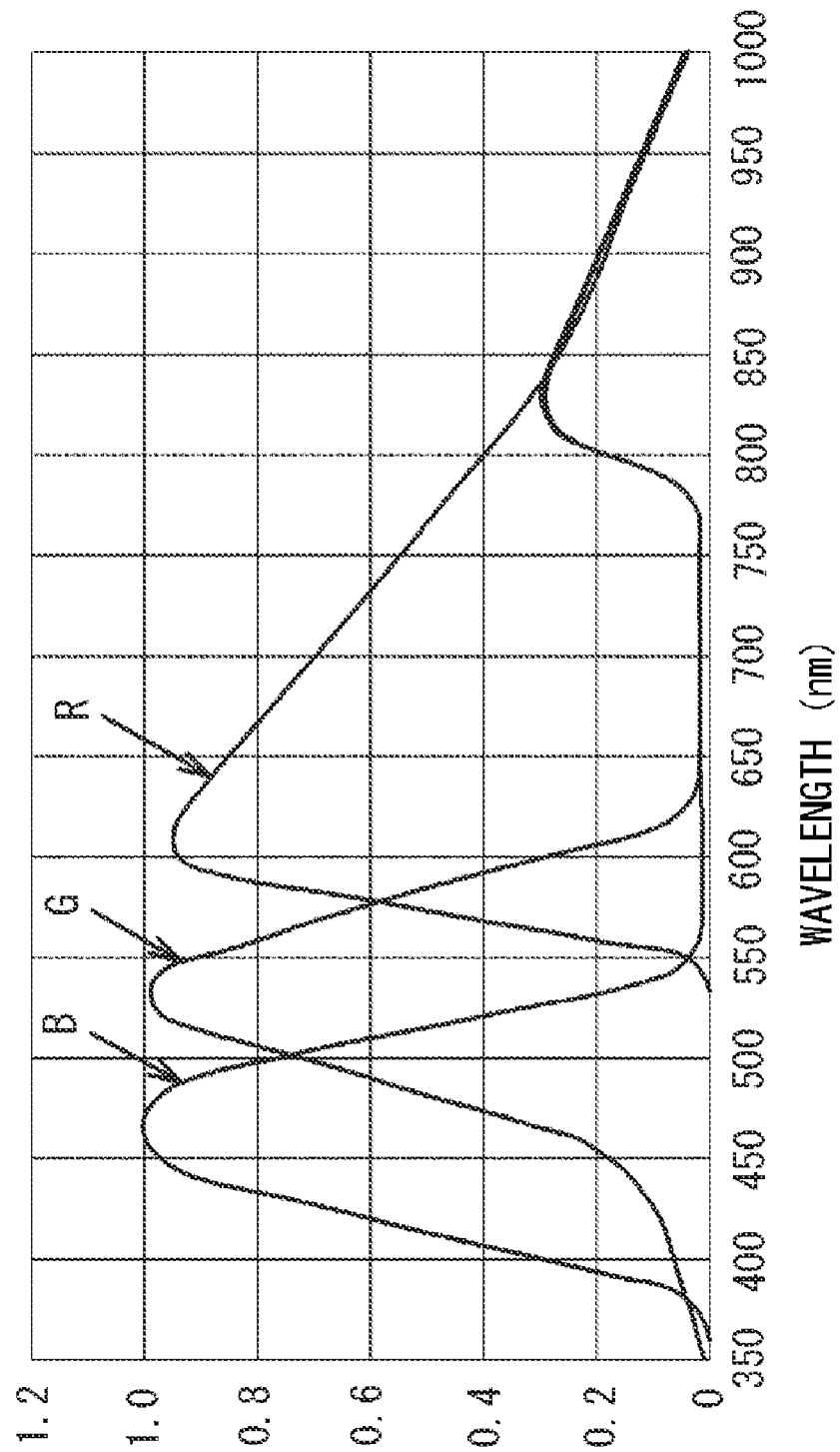
FIG. 5 is a graph illustrating sensitivity characteristics of an imaging unit in the fundus camera according to an exemplary embodiment of the present invention.

FIG. 5 is a graph illustrating a sensitivity characteristic of the imaging unit 7. The imaging unit 7 has sensitivity to both light of a visible light region and light of a near-infrared light region. The imaging unit 7 has characteristics of being capable of outputting both a moving image and a still image.

Figure 6B:
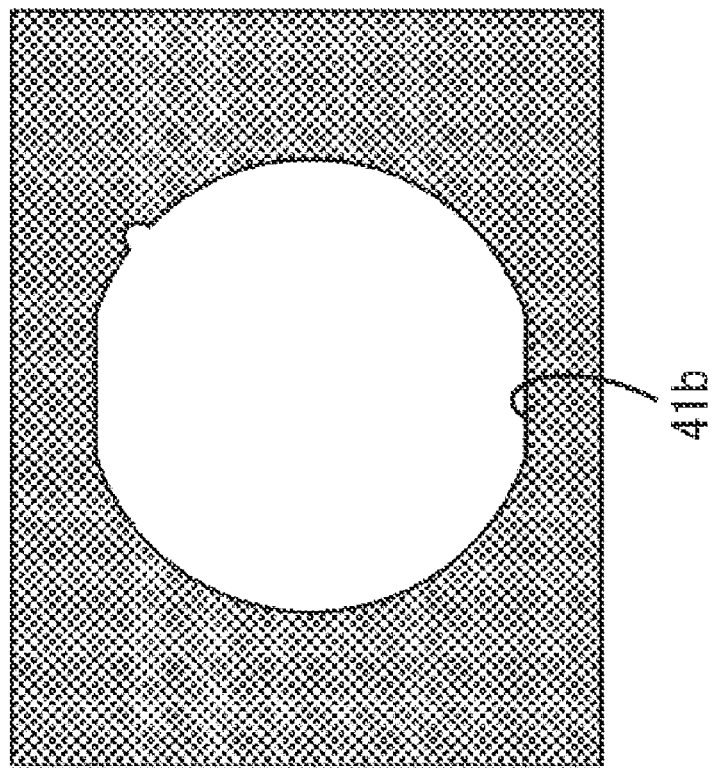
FIGS. 6A and 6B illustrate shapes of aperture masks.
Figure 6A:
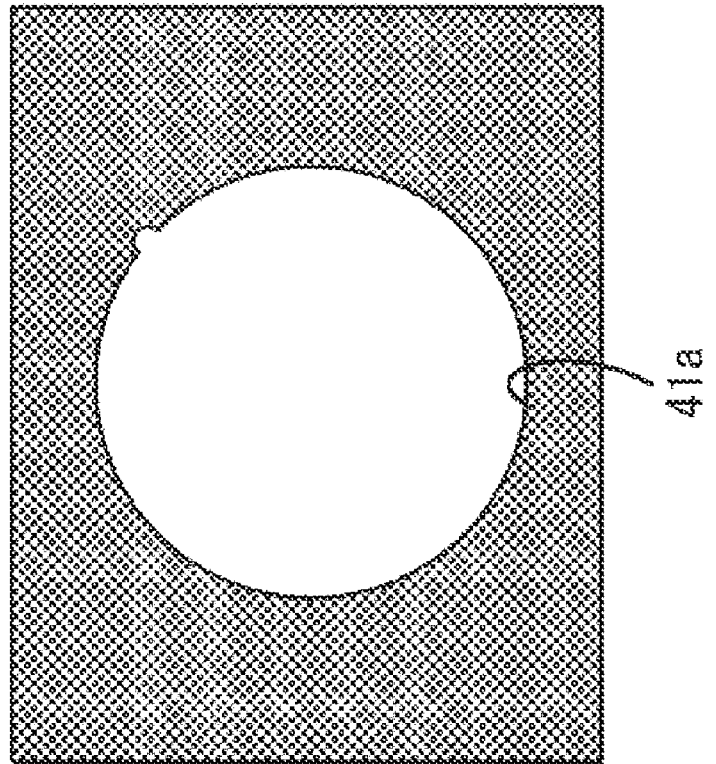

An image including a moving image or a still image photographed by the imaging unit 7 is displayed on the monitor 32. In a case where a fundus is observed and photographed with near-infrared light, an image to be displayed on the monitor 32 is obtained by adding an aperture mask 41a, which is electronically generated for observing the fundus with near-infrared light, to a moving image or a still image of the fundus by the imaging unit 7, as illustrated in FIG. 6A. Then, the obtained image is displayed on the monitor 32, which can be observed with visible light via the optical finder 23. In a case where a still image of the fundus is observed and photographed with visible light, an image to be displayed on the monitor 32 is obtained by adding an aperture mask 41b, which is electronically generated for observing the fundus with visible light, to a still image of the fundus by the imaging unit 7, as illustrated in FIG. 6B.

The shape of the aperture mask varies with observation modes, i.e., a visible light observation mode and a near-infrared light observation mode. This is because a photographing angle of view in the case of observing/photographing a fundus with visible light is larger than that in the case of observing/photographing a fundus with near-infrared light. Thus, the diameter of the aperture mask 41a for observing a fundus with near-infrared light is equal to a vertical dimension of the aperture mask 41b for observing a fundus with visible light. The horizontal dimension of the aperture mask 41b is larger than that of the aperture mask 41a.

In a case where a fundus $E_r$ of a subject's eye E is observed and photographed in a non-mydriatic mode, the illumination optical system uses light of a near-infrared wavelength as illumination light for observing the fundus. Thus, the visible light cut filter 10 is inserted into the optical path of the illumination optical system to thereby cut off light of a visible light region. In addition, the cornea diaphragm 20a and the crystalline lens diaphragm 15a to be used for observing a fundus with invisible light are inserted into the optical path.

The control unit 33 retreats the near-infrared cut filter 18 out of the optical path. In the observing/photographing optical system, the control unit 33 inserts the quick-return mirror 6 into the optical path. Further, the control unit 33 causes the internal fixation target 22 to turn on. In addition, the control unit 33 withdraws the oblique mirror 21 out of the optical path. Furthermore, the control unit 33 drives the imaging unit 7 at low resolution while increasing a gain, i.e., an amplification factor, as compared with the time of photographing a still image of the fundus. The reasons for performing such setting is that the contrast of an image of the fundus observed with near-infrared observing light at the time of photographing a moving image of the fundus is low, that the sensitivity of the imaging unit is low in the case of using near-infrared observing light, as compared with the case of using light of a visible light region, that it is better to increase the gain even though a signal-to-noise (S/N) ratio is sacrificed, and that high resolution is unnecessary.

As described above, the aperture mask 41a for observing a fundus with near-infrared light is selected for a photographed reflection image of a fundus. An examiner can move the internal fixation target 22 while observing a moving image output from the imaging unit 7 on the monitor 32. Thus, the examiner guides a line of sight of a subject's eye E to a desired position. Then, focusing is performed by moving the focusing lens 4 while alignment is performed. Thus, a still image of the fundus is photographed by pushing a photographing switch (not shown).

When a still image of a fundus is photographed, a sufficient amount of light for photographing the fundus can be obtained using flash light of the xenon tube 12. In addition, high resolution is needed because a photographed still image of the fundus is used for diagnosis. Accordingly, when a still image of a fundus is photographed, the control unit 33 performs a control operation of restoring the gain and the resolution of the imaging unit 7.

In order to generate visible photographing light, the control unit 33 inserts the near-infrared cut filter 18 into the optical path and removes the visible light cut filter 10 therefrom. Then, the control unit 33 causes the quick-return mirror 6 to retreat out of the optical path. Subsequently, the control unit 33 causes the xenon tube 12 to emit light. Then, the photographing of the fundus is performed. A photographed color image is displayed on the monitor 32.

In the mydriatic mode, in which a mydriatic is applied to the subject's eye for observation and photographing of the subject's eye fundus, the examiner uses a lever (not shown) and inserts the oblique mirror 21 into the optical path. In order to generate visible observing light, the control unit 33 causes the visible light cut filter 10 to retreat out of the optical path. Then, the control unit 33 inserts the near-infrared cut filter 18 and the quick-return mirror 6 into the optical path. Further, the internal fixation target 22 is turned off. Furthermore, the control unit 33 changes the cornea diaphragm 20a and the crystalline diaphragm 15a to the cornea diaphragm 20b and the crystalline diaphragm 15b, respectively, and selects the aperture mask 41b.

Because the visible light cut filter 10 is withdrawn from the optical path, the examiner can observe the fundus $E_r$ of the subject's eye E by direct vision via the optical finder 23 with visible light using the halogen lamp 9. Further, the examiner uses the external fixation target 24, which is placed outside the optical system, for performing a fixation guiding operation for the subject's eye E.

When the examiner pushes the photographing switch, the control unit 33 sets the gain and the resolution of the imaging unit 7 at values for photographing a still image of a fundus. Then, the control unit 33 causes the quick-return mirror 6 to retreat out of the optical path. Further, the control unit 33 causes the xenon tube 12 to emit light. Thus, photographing of the fundus is performed. A photographed color image is displayed on the monitor 32, similarly to the case where a fundus is observed with near-infrared light and is photographed with visible light.

Thus, the examiner switches between a near-infrared light observation mode and a visible light observation mode by operating the oblique mirror 21. However, the examiner can switches between the near-infrared light observation mode and the visible light observation mode by changing the visible light cut filter 10. At that time, the control unit 33 inserts or removes the oblique mirror 21 into or from the optical path. Alternatively, the oblique mirror 21 can be constructed not to totally reflect light of the internal fixation target 22 and but to have a light flux distributing function of distributing and transmitting apart of light having the wavelength of light of the internal fixation target 22. Consequently, the insertion/removal of the oblique mirror 21 is unnecessary.

Further, data representing the amount of deviation between the position of an optical axis at observation of a fundus and that of the optical axis at photographing of the fundus, which has been described with reference to FIG. 3, can preliminarily be input to the display position correcting unit 31. Thus, when a photographed image is displayed on the monitor 32, the control unit 33 can perform a control operation of displaying the photographed image at a position offset based on the amount of deviation. Consequently, occurrence of the deviation between the position at which an observation moving image is displayed and the position at which a photographed still image is displayed can be prevented. Accordingly, needs for reducing the thickness t of the quick-return mirror 6 and for cross-sectionally shaping the quick-return mirror 6 like a wedge are eliminated.

Further, according to the present embodiment, the aperture masks 41a and 41b are electronically created. However, a substantial aperture mask can be provided by increasing the number of forming fundus images using, e.g., a relay lens in the observing/photographing system. Thus, the aperture mask can mechanistically be changed. In accordance with the fundus camera according to an exemplary embodiment of the present invention, both the observation of a near-infrared moving image and the photographing of a visible light still image can be achieved using the imaging unit that has sensitivity to both light of a visible wavelength region and light of a near-infrared wavelength region. Consequently, the device can be miniaturized.

Further, the quick-return mirror having characteristics adapted to transmit near-infrared light and to reflect light of a visible light region is used as the optical path splitting unit for splitting an optical path from a subject's eye fundus into an optical path to the imaging unit and an optical path to the internal fixation target. Thus, when the fundus is observed with near-infrared light, the internal fixation target can efficiently be indicated to the subject's eye. In addition, when a still fundus image is photographed, the quick-return mirror is retreated from the optical path. Thus, loss of the amount of reflection light from the fundus is not caused by the optical path splitting unit.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

What is claimed is:

1. An ophthalmologic apparatus for imaging light returning from a subject's eye illuminated via an illumination optical system on an imaging unit via a photographing optical system and capturing an image of the subject's eye, the ophthalmologic apparatus comprising:
    an optical path splitting unit located in the photographing optical system, having characteristics of reflecting at least a part of light of a visible region and of transmitting light of a near-infrared region;
    wherein the imaging unit has sensitivity to both light of a visible region and light of a near-infrared region.

2. The ophthalmologic apparatus according to claim 1, further comprising:
    a focusing unit located in the photographing optical system and configured to adjust focus on the subject's eye,
    wherein the optical path splitting unit is located between the focusing unit and the imaging unit.

3. The ophthalmologic apparatus according to claim 1, further comprising:
    an internal fixation target indicating unit located at a position substantially conjugate with a position of a fundus of the subject's eye on a reflection optical path of the optical path splitting unit and configured to guide a direction of a line of sight of the subject's eye,
    wherein the imaging unit is capable of outputting a moving image and a still image, and captures a fundus image formed from reflection light from the fundus.

4. The ophthalmologic apparatus according to claim 1, wherein the imaging unit outputs an image based on the transmitted light of the near-infrared region through the optical path splitting unit in a case where the optical path splitting unit is inserted into an optical path of the photographing optical system, and the imaging unit outputs an image based on the light of the visible region in a case where the optical path splitting unit is retreated from the optical path.

5. An ophthalmologic system comprising:
    an ophthalmologic apparatus for imaging light returning from a subject's eye illuminated via an illumination optical system on an imaging apparatus via a photographing optical system, the ophthalmologic apparatus having an optical path splitting unit that is located in the photographing optical system, and that has characteristics of reflecting at least part of light of a visible region and of transmitting light of a near-infrared region,
    wherein the imaging apparatus is located in the photographing optical system, captures an image of the subject's eye, and has sensitivity to both light of a visible region and light of a near-infrared region.

6. The ophthalmologic system according to claim 5,
    wherein the imaging apparatus outputs an image based on the transmitted light of the near-infrared region through the optical path splitting unit in a case where the optical path splitting unit is inserted into an optical path of the photographing optical system, and the imaging apparatus outputs an image based on the light of the visible region in a case where the optical path splitting unit is retreated from the optical path.

7. The ophthalmologic system according to claim 5, further comprising:
    an internal fixation target indicating unit located at a position substantially conjugate with a position of a fundus of the subject's eye on a reflection optical path of the optical path splitting unit and configured to guide a direction of a line of sight of the subject's eye,
    wherein the imaging apparatus is capable of outputting a moving image and a still image, and captures a fundus image formed from reflection light from the fundus.

8. The ophthalmologic apparatus according to claim 5, further comprising a control apparatus configured to increase gain of the imaging apparatus in a case where the imaging apparatus outputs an image based on the transmitted light of the near-infrared region through the optical path splitting unit.

9. An ophthalmologic apparatus for imaging light returning from a fundus of a subject's eye illuminated via an illumination optical system on an imaging unit via a photographing optical system and capturing an image of the fundus, the ophthalmologic apparatus comprising:

an optical path splitting unit located in the photographing optical system, having characteristics of reflecting at least part of light of a visible region and of transmitting light of a near-infrared region; and an internal fixation target indicating unit located at a position substantially conjugate with a position of the fundus on a reflection optical path of the optical path splitting unit and configured to guide a direction of a line of sight of the subject's eye.

10. The ophthalmologic apparatus according to claim 9, wherein the internal fixation target indicating unit is turned on during observing of the fundus with light of a near-infrared region and the internal fixation target is turned off during observing of the fundus with light of a visible region.

11. The ophthalmologic apparatus according to claim 9, wherein the optical path splitting unit is inserted into an optical path of the photographing optical system during observing of the fundus and the optical path splitting unit is retreated from the optical path during photographing of the fundus image with the light of the visible region.

12. The ophthalmologic apparatus according to claim 9, further comprising an external fixation target indicating unit, wherein the external fixation target indicating unit is turned on during observing of the fundus with light of a visible region.

13. An ophthalmologic apparatus for imaging light returning from a fundus of a subject's eye illuminated via an illumination optical system on an imaging unit via a photographing optical system and capturing an image of the fundus, the ophthalmologic apparatus comprising:

an optical path splitting unit located in the photographing optical system, having characteristics of reflecting light of a visible region and of transmitting light of a near-infrared region, wherein the illumination optical system includes:
a near-infrared light generating unit configured to irradiate light of a near-infrared region;
a visible light generating unit configured to irradiate light of a visible region; and
wherein the optical path splitting unit is inserted into an optical path of the photographing optical system in a case where the near-infrared light generating unit irradiates the light of the near-infrared region and the optical path splitting unit is retreated from the optical path in a case where the visible light generating unit irradiates the light of the visible region.

14. An ophthalmologic apparatus for imaging light returning from a subject's eye illuminated via an illumination optical system on an imaging unit via a photographing optical system and capturing an image of the subject's eye, the ophthalmologic apparatus comprising:

an optical path splitting unit located in the photographing optical system, having characteristics of reflecting light of a visible region and of transmitting light of a near-infrared region;

a diaphragm unit provided in the illumination optical system, having first and second diaphragms differing in diameter; and a control unit configured to change between the first and second diaphragms based on inserting or retreating of the optical path splitting unit.

15. The ophthalmologic apparatus according to claim 14, wherein a diameter of the second diaphragm is larger than that of the first diaphragm, and wherein the first diaphragm is inserted into an optical path of the illumination optical system in a case where the optical path splitting unit is inserted into an optical path of the photographing optical system, and the second diagram is inserted into the optical path of the illumination optical system in a case where the optical path splitting unit is retreated from the optical path of the photographing optical system.

16. An ophthalmologic apparatus for imaging light returning from a subject's eye illuminated via an illumination optical system on an imaging unit via a photographing optical system and capturing an image of the subject's eye, the ophthalmologic apparatus comprising:

an optical path splitting unit located in the photographing optical system, having characteristics of reflecting light of a visible region and of transmitting light of a near-infrared region; and a control unit configured to change between first and second aperture masks to be added to the image based on inserting or retreating of the optical path splitting unit.

17. The ophthalmologic apparatus according to claim 16, wherein the second aperture mask is larger than the first aperture mask, and wherein the first aperture mask is added to the image based on the transmitting light of near-infrared region in a case where the optical path splitting unit is inserted into an optical path of the photographing optical system, and the first aperture mask is added to the image based on the light of the visible region in a case where the optical path splitting unit is retreated from the optical path.

* * * * *